United States Patent [19]

Fujino et al.

[11] Patent Number: 5,952,503
[45] Date of Patent: Sep. 14, 1999

[54] METHOD FOR PRODUCING OPTICALLY-ACTIVE 2-PIPERAZINECARBOXYLIC ACID DERIVATIVES

[75] Inventors: Toshihiro Fujino, Kuwana; Haruyo Sato, Nagoya, both of Japan

[73] Assignee: Toray Industries, Inc., Japan

[21] Appl. No.: 09/125,840

[22] PCT Filed: Dec. 27, 1996

[86] PCT No.: PCT/JP96/03864

§ 371 Date: Aug. 26, 1998

§ 102(e) Date: Aug. 26, 1998

[87] PCT Pub. No.: WO98/29398

PCT Pub. Date: Jul. 9, 1998

[51] Int. Cl.⁶ .................................................. C07D 241/04
[52] U.S. Cl. ............................................ 544/389; 544/390
[58] Field of Search ........................................ 544/389, 390

[56] References Cited

U.S. PATENT DOCUMENTS 5,413,999  5/1995  Vacca et al. .......................... 541/231.5

*Primary Examiner*—Samuel Barts
*Attorney, Agent, or Firm*—Austin R. Miller

[57] ABSTRACT

Optically-active 2-piperazinecarboxylic acid derivatives are produced through diastereomer salt resolution using optically-active acidic amino acid derivative as the resolving reagent. In this method, the recovery of the resolving reagent used is high, and the production efficiency to produce the optically-active products is high.

As the optically-active acidic amino acid derivatives, usable are optically-active, N-acylated acidic amino acid derivatives and optically-active, N-sulfonylated acidic amino acid derivatives.

8 Claims, No Drawings

METHOD FOR PRODUCING OPTICALLY-ACTIVE 2-PIPERAZINECARBOXYLIC ACID DERIVATIVES

This application is a 371 of PCT/JP96/03864 filed Dec. 27, 1996.

TECHNICAL FIELD

The present invention relates to an industrial method for producing optically-active 2-piperazinecarboxylic acid derivatives which are useful as intermediate materials for drugs.

BACKGROUND ART

For producing optically-active 2-piperazinecarboxylic acid derivatives, for example, known are 1) a method of optical resolution using L-pyroglutamic acid as the resolving reagent (WO 95-21162), 2) a method of optical resolution using an optically-active α-hydroxy acid such as L-malic acid or the like as the resolving reagent (WO 95-29170), 3) a method of optical resolution using N-tosyl-L-phenylalanine as the resolving reagent (EP 710652), etc. However, as their solubility in water is high, the resolving reagents to be used in 1) and 2) are defective in that their recovery after use is low. On the other hand, as its solubility in acidic aqueous solutions is low, N-tolyl-L-phenylalanine to be used in 3) has the advantage of high recovery after use, but has the disadvantage of low production efficiency in that its ability to dissolve diastereomer salts is low and therefore the salt concentration in the resolving step using it could not be high, and that it requires expensive phenylalanine.

The present invention is to provide a method for producing optically-active 2-piperazinecarboxylic acid derivatives through diastereomer salt resolution, in which the recovery of the resolving reagent used is high and the production efficiency to give the products is high.

DISCLOSURE OF THE INVENTION

We, the present inventors have assiduously studied to obtain industrial methods for producing optically-active 2-piperazinecarboxylic acid derivatives, and, as a result, have found out that our object can be attained by using chemically-modified derivatives of inexpensive and easily-available, optically-active acidic amino acid derivatives as the resolving reagent for optically resolving 2-piperazinecarboxylic acid derivatives.

Specifically, the present invention is a method for producing optically-active 2-piperazinecarboxylic acid derivatives, which is characterized in that a 2-piperazinecarboxylic acid derivative is optically resolved with a resolving reagent of an optically-active acidic amino acid derivative such as an optically-active, N-acylated acidic amino acid derivative, an optically-active, N-sulfonylated acidic amino acid derivative or the like.

The resolving reagent, optically-active acidic amino acid derivative for use in the invention has 2 or more carboxyl groups and an amino group in the molecule, and includes, for example, optically-active, N-acylated acidic amino acid derivatives, optically-active, N-sulfonylated acidic amino acid derivatives, etc. Concretely, it may be selected from N-acylated derivatives and N-sulfonylated derivatives of optically-active aspartic acid and optically-active glutamic acid, and any of D-forms and L-forms of those derivatives may be used in accordance with the object.

As the optically-active N-acylated derivatives, usable are optically-active acidic amino acid derivatives of the following general formula (I):

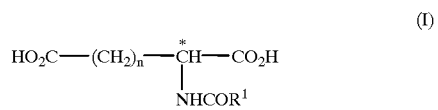

(I)

wherein $R^1$ represents i) a hydrogen atom, ii) an unsubstituted or halogen-substituted, linear or branched alkyl group having from 1 to 10 carbon atoms, iii) an unsubstituted aryl group, or an aryl group substituted by an alkyl group having from 1 to 10 carbon atoms, an alkoxyl group having from 1 to 10 carbon atoms, a halogen atom or a hydroxyl group, iv) an aralkyl group of which the aromatic ring moiety is unsubstituted or substituted by an alkyl group having from 1 to 10 carbon atoms, an alkoxyl group having from 1 to 10 carbon atoms, a halogen atom or a hydroxyl group, or v) an aralkyloxy group of which the aromatic ring moiety is unsubstituted or substituted by an alkyl group having from 1 to 10 carbon atoms, an alkoxyl group having from 1 to 10 carbon atoms, a halogen atom or a hydroxyl group; and n represents 1 or 2. As their specific examples, mentioned are acetylaspartic acid, formylglutamic acid, isobutyroylaspartic acid, benzoylaspartic acid, benzoylglutamic acid, para-toluoylaspartic acid, paratoluoylglutamic acid, paranitrobenzoylaspartic acid, paranitrobenzoylglutamic acid, parachlorophenylacetylaspartic acid, benzyloxycarbonylaspartic acid, benzyloxycarbonylglutamic acid, etc.

As the optically-active N-sulfonylated derivatives, usable are those of the following general formula (II):

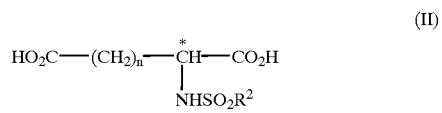

(II)

wherein $R^2$ represents i) an unsubstituted or halogen-substituted, linear or branched alkyl group having from 1 to 10 carbon atoms, ii) an unsubstituted aryl group, or an aryl group substituted by an alkyl group having from 1 to 10 carbon atoms, an alkoxyl group having from 1 to 10 carbon atoms, a halogen atom or a hydroxyl group, or iii) an aralkyl group of which the aromatic ring moiety is unsubstituted or substituted by an alkyl group having from 1 to 10 carbon atoms, an alkoxyl group having from 1 to 10 carbon atoms, a halogen atom or a hydroxyl group; and n represents 1 or 2. As their specific examples, mentioned are methanesulfonylaspartic acid, methanesulfonylglutamic acid, benzenesulfonylaspartic acid, benzenesulfonylglutamic acid, paratoluenesulfonylaspartic acid, paratoluenesulfonylglutamic acid, paranitrobenzenesulfonylaspartic acid, paranitrobenzenesulfonylglutamic acid, parachlorobenzenesulfonylaspartic acid, parachlorobenzenesulfonylglutamic acid, etc.

These optically-active acidic amino acid derivatives can be easily produced from inexpensive aspartic acid and glutamic acid in any known methods. While recovered after use for resolution, they decompose or racemize little in acidic or neutral conditions at room temperature to 50° C.

The 2-piperazinecarboxylic acid derivatives to be optically resolved in the invention include, for example, those of the following general formula (IV):

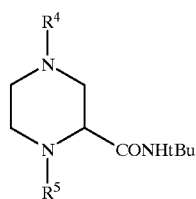

(IV)

wherein $R^4$ and $R^5$ may be the same or different, and each represents i) a hydrogen atom, ii) an alkyl group having from 1 to 10 carbon atoms, iii) an unsubstituted aryl group, or an aryl group substituted by an alkyl group having from 1 to 10 carbon atoms, an alkoxyl group having from 1 to 10 carbon atoms, a nitro group or a halogen atom, or iv) an aralkyl group of which the aromatic ring moiety is unsubstituted or substituted by an alkyl group having from 1 to 10 carbon atoms, an alkoxyl group having from 1 to 10 carbon atoms, a nitro group or a halogen atom; and tBu represents a tert-butyl group; and a 2-piperazinecarboxylic acid derivative of the following general formula (V):

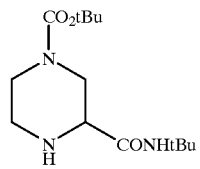

(V)

wherein tBu represents a tert-butyl group. Especially preferred is N-tert-butyl-2-piperazinecarboxamide of the following general formula (VI):

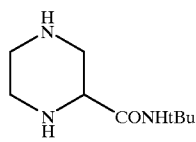

(VI)

wherein tBu represents a tert-butyl group.

2-Piperazinecarboxylic acid derivatives which are used as the raw materials in the invention can be produced in any known methods. For example, they can be produced by hydrogenation of pyrazinecarboxylic acid derivatives, or by condensation for cyclization of N,N-dialkylethylenediamines with 2,3-dihalopropionates followed by chemical modification of the resulting condensates.

The 2-piperazinecarboxylic acid derivatives to be used herein as the raw materials include not only racemic mixtures composed of (+)-2-piperazinecarboxylic acid derivative and (−)-2-piperazinecarboxylic acid derivative in a ratio of 1/1, but also any other mixtures thereof where the amount of any one of the optical isomers is larger than that of the other.

BEST MODES OF CARRYING OUT THE INVENTION

Preferred procedures and conditions for optical resolution of 2-piperazinecarboxylic acid derivatives according to the invention are mentioned below.

From 0.4 to 1.1 mols, but preferably from 0.5 to 1.0 mol of the resolving reagent selected from optically-active, N-acylated acidic amino acid derivatives and optically-active, N-sulfonylated acidic amino acid derivatives is contacted with 1 mol of a 2-piperazinecarboxylic acid derivative in a solvent to form diastereomer salts. In this step, any of mineral acids such as hydrochloric acid, sulfuric acid and the like, or organic carboxylic acids such as formic acid, acetic acid and the like may be added to the resolution system. Preferably, the amount of the additional acid of such mineral acids and organic carboxylic acid acids is, as combined with the resolving reagent used, from 0.5 to 1.1 mols, more preferably from 0.6 to 1.0 mols, relative to 1 mol of the 2-piperazinecarboxylic acid derivative.

The solvent to be used herein may be any one that brings about selective precipitation of one of the optically-active diastereomer salts formed therein without chemically modifying both the 2-piperazinecarboxylic acid derivative and the resolving reagent therein. Preferably, the solvent is so selected that the diastereomer salts formed are dissolved therein to have a salt concentration of not smaller than 25% by weight. Concretely, for example, the solvent usable herein includes water, alcohols such as methanol, ethanol, 1-propanol, 2-propanol, 1-butanol, 2-butanol, tert-butanol, etc., and mixed solvents of these.

The salt concentration referred to herein indicates the concentration of the salts as formed by the 2-piperazinecarboxylic acid derivative being resolved and the resolving reagent used. Where the additional acid of mineral acids or organic carboxylic acids is added to the resolution system, the salt concentration shall correspond to the overall salt concentration as formed by the 2-piperazinecarboxylic acid derivative, the resolving reagent and the additional acid of mineral acids or organic carboxylic acids. Concretely, the salt concentration is represented by [(2-piperazinecarboxylic acid derivative+resolving reagent+additional acid of mineral acids or organic carboxylic acids)/total weight×100].

A higher salt concentration, if attained, is preferred in view of the economics of the resolution process, as the producibility per the volume of the reactor used is higher.

Any means is employable for contacting the resolving reagent with a 2-piperazinecarboxylic acid derivative to be resolved therewith. For example, a 2-piperazinecarboxylic acid derivative and a resolving reagent may be added to the solvent all at a time, or may be added thereto separately. If desired, salts are previously formed from a 2-piperazinecarboxylic acid derivative and a resolving agent, and they may be added to the solvent. The additional salt of mineral acids or organic carboxylic acids, if used, may be added to the solvent along with the 2-piperazinecarboxylic acid derivative and the resolving reagent all at a time, or may be added thereto separately. No special order is defined for the addition of those substances to the solvent.

The thus-formed, diastereomer salts-containing solution is heated so as to dissolve the salts in the solvent, and thereafter cooled and/or concentrated to thereby make the hardly-soluble diastereomer salt precipitated in the solution.

The temperature at which the hardly-soluble diastereomer salt is precipitated in the solution may fall within the range between the solidifying point and the boiling point of the solvent used, and may be selected within the range in accordance with the intended object, but, in general, it preferably falls between 0° C. and 100° C.

The crystal of the hardly-soluble diastereomer salt can be easily separated through ordinary solid-liquid separation such as filtration, centrifugation or the like. Recrystallization of the crystal separated gives the intended, high-purity diastereomer salt.

The thus-obtained diastereomer salt is de-salted in a suitable manner to decompose it into the (+)-2-piperazinecarboxylic acid derivative or (−)-2-piperazinecarboxylic acid derivative and the resolving reagent, which are separately collected.

For de-salting the diastereomer salt, employable is any ordinary method. For example, the salt may be processed with an acid or alkali in an aqueous solvent, or it may be processed with an ion-exchange resin. In one embodiment, the diastereomer salt is de-salted in water, to which is added an aqueous alkaline solution of sodium hydroxide or the like, and then extracted with an organic solvent such as dichloromethane or the like, whereby the constituent, 2-piperazinecarboxylic acid derivative is extracted into the organic layer. The resulting extract is concentrated and crystallized to obtain the intended, optically-active 2-piperazinecarboxylic acid derivative. Next, a mineral acid such as hydrochloric acid, sulfuric acid or the like is added to the extraction residue of the aqueous layer to make it have a pH of from 1 to 2, and the resolving reagent used is taken out of the aqueous layer through filtration. Alternatively, the resolving reagent may be recovered through extraction of the aqueous layer with an organic solvent such as dichloromethane or the like.

The resolving reagent used in the present invention can be recovered at a high yield in any ordinary de-salting method, and is racemated little during the recovering step. In other words, as still having the optical activity, the resolving reagent recovered can be re-used in the optical resolution of the invention.

The optically-active 2-piperazinecarboxylic acid derivatives obtained according to the invention are useful as intermediates for drugs.

EXAMPLES

The invention is described in more detail with reference to the following Examples, which, however, are not intended to restrict the scope of the invention.

The optical purity of the 2-piperazinecarboxamides constituting the diastereomer salts obtained in the following Examples was determined, for example, according to the method mentioned below. The diastereomer salt crystal formed was de-salted in 10% aqueous ammonia of being 5 molar times the constituent, N-tert-butyl-2-piperazinecarboxamide, and then stirred with dichloromethane for 10 minutes. Next, this was subjected to liquid-liquid separation, then the resulting dichloromethane layer was dried with anhydrous magnesium sulfate, and thereafter dichloromethane was evaporated out to obtain a crude product, optically-active N-tert-butyl-2-piperazinecarboxamide. From 10 to 15 mg of this optically-active N-tert-butyl-2-piperazinecarboxamide was dissolved in 10 ml of acetonitrile. To 0.1 ml of the resulting solution, added was 1 ml of a solution of 400 mg of O,O'-di-p-toluoyl-L-tartaric anhydride as dissolved in 100 ml of acetonitrile. While being kept as such for about 10 minutes, N-tert-butyl-2-piperazinecarboxamide was reacted with O,O'-di-p-toluoyl-L-tartaric anhydride. 1 ml of a solution of 0.2 g of 85% phosphoric acid as dissolved in 100 ml of water was added to the reaction mixture, and left as such for about 10 minutes, whereby the excess O,O'-di-p-toluoyl-L-tartaric anhydride was hydrolyzed. 5 µl of the resulting mixture was analyzed through HPLC, in which the column used was CAPCELL PAK C18 SG120 (of Shiseido) and the mobile phase was aqueous 0.04% phosphoric acid/acetonitrile=30/70 (v/v). The column temperature was 25° C.; the flow rate was 0.7 ml/min; and the eluates were detected with UV (210 nm). The diastereomer resulting from the reaction of (+)-N-tert-butyl-2-piperazinecarboxamide and O,O'-di-p-toluoyl-L-tartaric anhydride was detected at a retention time of 7.3 minutes, and that from the reaction of (−)-N-tert-butyl-2-piperazinecarboxamide and O,O'-di-p-toluoyl-L-tartaric anhydride was detected at a retention time of 8.8 minutes. The optical purity of 2-piperazinecarboxamides and 2-piperazinecarboxylates of which the 1- and 4-positioned hydrogen atoms were substituted with benzyl groups or the like was determined through high-performance liquid chromatography using a CHIRALCEL CD column (manufactured by Daisel Chemical Industry).

Example 1

27.8 g (0.15 mole) of (±)-N-tert-butyl-2-piperazinecarboxamide (this is hereinafter referred to as "(±)-BPCA"), 45.2 g (0.15 mole) of N-tosyl-D-glutamic acid, and 90 g of water were put into a 1-liter four-neck flask equipped with a thermometer, a condenser and a stirrer, and heated therein at 50° C. After having been stirred at 50° C. for 1 hour, this was cooled to 30° C. over a period of 4 hours. After having been further stirred at 30° C. for 2 hours, this was filtered to collect 37.3 g of white crystal of the diastereomer salt formed. The optical purity of (+)-BPCA in the crystal was 95.0% e.e., and the yield thereof relative to (+)-BPCA having originally existed in the starting racemate was 70.2%. The concentration of the diastereomer salt formed was 44.7% by weight.

Example 2

27.8 g (0.15 mole) of (±)-BPCA, 43.1 g (0.15 mole) of N-benzenesulfonyl-L-glutamic acid, and 75 g of water were put into a 1-liter four-neck flask equipped with a thermometer, a condenser and a stirrer, and heated therein at 62° C. After having been stirred at 62° C. for 1 hour, this was cooled to 30° C. over a period of 5 hours. After having been further stirred at 30° C. for 2 hours, this was filtered to collect 32.7 g of white crystal of the diastereomer salt formed. The optical purity of (−)-BPCA in the crystal was 72.1% e.e., and the yield thereof relative to (−)-BPCA having originally existed in the starting racemate was 71.7%. The concentration of the diastereomer salt formed was 48.6% by weight.

Example 3

18.5 g (0.10 mole) of (±)-BPCA, 13.7 g (0.05 mole) of N-benzenesulfonyl-L-aspartic acid, 1.8 g (0.05 mole) of hydrochloric acid and 60 g of 80 wt. % methanol were put into a 1-liter four-neck flask equipped with a thermometer, a condenser and a stirrer, and heated therein at 71° C. After having been stirred at 71° C. for 1 hour, this was cooled to 30° C. over a period of 3 hours. After having been further stirred at 30° C. for 2 hours, this was filtered to collect 20.0 g of white crystal of the diastereomer salt formed. The optical purity of (−)-BPCA in the crystal was 96.3% e.e., and the yield thereof relative to (−)-BPCA having originally existed in the starting racemate was 82.1%. The concentration of the diastereomer salt formed was 36.3% by weight.

Example 4

50.0 g (0.27 mole) of (±)-BPCA, 76.2 g (0.27 mole) of N-p-nitrobenzoyl-L-aspartic acid and 600 ml of methanol were put into a 1-liter four-neck flask equipped with a thermometer, a condenser and a stirrer, and heated therein at 55° C. After having been stirred at 55° C. for 1 hour, this was cooled to 20° C. over a period of 4 hours. After having been further stirred at 20° C. for 2 hours, this was filtered to collect 54.0 g of white crystal of the diastereomer salt formed. The optical purity of (+)-BPCA in the crystal was 69.3% e.e., and the yield thereof relative to (+)-BPCA having originally existed in the starting racemate was 72.4%.

Example 5

50.0 g (0.27 mole) of (±)-BPCA, 72.1 g (0.27 mole) of N-benzyloxycarbonyl-L-aspartic acid and 1500 ml of methanol were put into a 2-liter four-neck flask equipped with a thermometer, a condenser and a stirrer, and heated therein at 55° C. After having been stirred at 55° C. for 1 hour, this was cooled to 20° C. over a period of 4 hours. After having been further stirred at 20° C. for 2 hours, this was filtered to collect 22.0 g of white crystal of the diastereomer salt formed. The optical purity of (−)-BPCA in the crystal was 56.4% e.e., and the yield thereof relative to (−)-BPCA having originally existed in the starting racemate was 28.1%.

Example 6

50.0 g (0.27 mole) of (±)-BPCA, 77.6 g (0.27 mole) of N-benzenesulfonyl-L-glutamic acid and 400 ml of water were put into a 1-liter four-neck flask equipped with a thermometer, a condenser and a stirrer, and heated therein at 60° C. After having been stirred at 60° C. for 1 hour, this was cooled to 20° C. over a period of 4 hours. After having been further stirred at 20° C. for 2 hours, this was filtered to collect 22.0 g of white crystal of the diastereomer salt formed. The optical purity of (−)-BPCA in the crystal was 96.0% e.e., and the yield thereof relative to (−)-BPCA having originally existed in the starting racemate was 33.8%.

INDUSTRIAL APPLICABILITY

Optically resolving 2-piperazinecarboxylic acid derivatives with a resolving reagent of optically-active acidic amino acid derivatives produces optically-active 2-piperazinecarboxylic acid derivatives at high yields. In this, in addition, the recovery of the resolving reagent used is high, and the concentration of the diastereomer salts formed is also high. The production efficiency of the method of producing optically-active 2-piperazinecarboxylic acid derivatives of the invention is high.

We claim:
1. A method for producing optically-active 2-piperazinecarboxylic acid derivatives, which comprises optically resolving 2-piperazinecarboxylic acid derivatives with a resolving reagent of optically-active acidic amino acid derivatives.

2. The method for producing optically-active 2-piperazinecarboxylic acid derivatives as claimed in claim 1, wherein the salt concentration is not lower than 25% by weight.

3. The method for producing optically-active 2-piperazinecarboxylic acid derivatives as claimed in claim 1 or 2, wherein the optically-active acidic amino acid derivatives are represented by the following general formula (I):

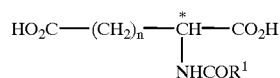

wherein $R^1$ represents i) a hydrogen atom, ii) an unsubstituted or halogen-substituted, linear or branched alkyl group having from 1 to 10 carbon atoms, iii) an unsubstituted aryl group, or an aryl group substituted by an alkyl group having from 1 to 10 carbon atoms, an alkoxyl group having from 1 to 10 carbon atoms, a halogen atom or a hydroxyl group, iv) an aralkyl group of which the aromatic ring moiety is unsubstituted or substituted by an alkyl group having from 1 to 10 carbon atoms, an alkoxyl group having from 1 to 10 carbon atoms, a halogen atom or a hydroxyl group, or v) an aralkyloxy group of which the aromatic ring moiety is unsubstituted or substituted by an alkyl group having from 1 to 10 carbon atoms, an alkoxyl group having from 1 to 10 carbon atoms, a halogen atom or a hydroxyl group; and n represents 1 or 2, or by the general formula II:

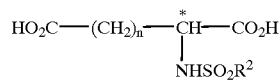

wherein $R^2$ represents i) an unsubstituted or halogen-substituted, linear or branched alkyl group having from 1 to 10 carbon atoms, ii) an unsubstituted aryl group, or an aryl group substituted by an alkyl group having from 1 to 10 carbon atoms, an alkoxyl group having from 1 to 10 carbon atoms, a halogen atom or a hydroxyl group, or iii) an aralkyl group of which the aromatic ring moiety is unsubstituted or substituted by an alkyl group having from 1 to 10 carbon atoms, an alkoxyl group having from 1 to 10 carbon atoms, a halogen atom or a hydroxyl group; and n represents 1 or 2.

4. The method for producing optically-active 2-piperazinecarboxylic acid derivatives as claimed in claim 3, wherein the optically-active acidic amino acid derivatives are represented by the following general formula (III):

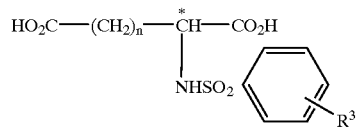

wherein $R^3$ represents i) a hydrogen atom, ii) a linear or branched alkyl group having from 1 to 4 carbon atoms, iii) a nitro group, or iv) a halogen atom; and n represents 1 or 2.

5. The method for producing optically-active 2-piperazinecarboxylic acid derivatives as claimed in claim 3, wherein the 2-piperazinecarboxylic acid derivatives are represented by the following general formula (IV):

(IV)

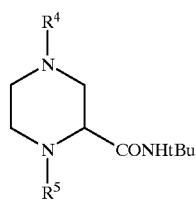

wherein $R^4$ and $R^5$ may be the same or different, and each represents i) a hydrogen atom, ii) an alkyl group having from 1 to 10 carbon atoms, iii) an unsubstituted aryl group, or an aryl group substituted by an alkyl group having from 1 to 10 carbon atoms, an alkoxyl group having from 1 to 10 carbon atoms, a nitro group or a halogen atom, or iv) an aralkyl group of which the aromatic ring moiety is unsubstituted or substituted by an alkyl group having from 1 to 10 carbon atoms, an alkoxyl group having from 1 to 10 carbon atoms, a nitro group or a halogen atom; and tBu represents a tert-butyl group.

6. The method for producing optically-active 2-piperazinecarboxylic acid derivatives as claimed in claim 5, wherein the 2-piperazinecarboxylic acid derivative is a compound of the following formula (VI):

(VI)

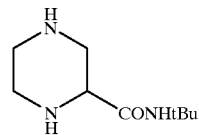

wherein tBu represents a tert-butyl group.

7. The method for producing optically-active 2-piperazinecarboxylic acid derivatives as claimed in claim 1, wherein the resolution solvent is water, or an alcohol, or a mixed solvent of water and an alcohol.

8. The method for producing optically-active 2-piperazinecarboxylic acid derivatives as claimed in claim 1, wherein the molar ratio of the resolving reagent to the 2-piperazinecarboxylic acid derivative is from 0.4/1 to 1.1/1.

* * * * *

UNITED STATES PATENT AND TRADEMARK OFFICE
CERTIFICATE OF CORRECTION

PATENT NO. : 5,952,503
DATED : September 14, 1999
INVENTOR(S) : Toshihiro Fujino It is certified that error appears in the above-identified patent and that said Letters Patent is hereby corrected as shown below:

In Column 2, line 53, after "2", please insert --, and preferably usable are those of the following general formula (III):

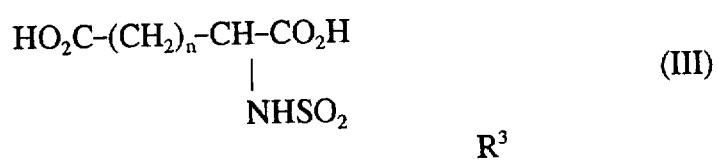

wherein $R^3$ represents I) a hydrogen atom, ii) a linear or branched alkyl group having from 1 to 4 carbon atoms, iii) a nitro group, or iv) a halogen atom; and n represents 1 or 2.--; and please delete "their".

In Column 3 at line 23 please delete "of the following general formula (V): and delete the following formula (V):

and at approximately line 35, please change "(VI)" to --(V)--; and at approximately line 38, please change "(VI)" to --(V)-- .

UNITED STATES PATENT AND TRADEMARK OFFICE
CERTIFICATE OF CORRECTION

PATENT NO. : 5,952,503
DATED : September 14, 1999
INVENTOR(S) : Toshihiro Fujino It is certified that error appears in the above-identified patent and that said Letters Patent is hereby corrected as shown below:

In Column 6, at line 12, please delete "and 2-piperazinecarboxylates"; and on line 15 please change "CD" TO - -OD- -.

In Column 10 at line 2 please change "(VI)" to - -(V)- -; and at approximately line 5, please change "(VI)" to -- (V) -- .

Signed and Sealed this

Tenth Day of April, 2001

Attest:

NICHOLAS P. GODICI

Attesting Officer     Acting Director of the United States Patent and Trademark Office